United States Patent
Bennett et al.

(10) Patent No.: US 6,225,293 B1
(45) Date of Patent: May 1, 2001

(54) METHODS AND COMPOUNDS FOR TRACKING THE BIODISTRIBUTION OF MACROMOLECULE-CARRIER COMBINATIONS

(75) Inventors: Clarence Frank Bennett; Muthiah Manoharan, both of Carlsbad; Normand Hebert, Cardiff by the Sea; Balkrishen Bhat, Carlsbad, all of CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/145,897

(22) Filed: Sep. 2, 1998

(51) Int. Cl.[7] .......................... A01N 43/04; A01N 61/00; C07H 19/00; C12Q 1/68
(52) U.S. Cl. ........................ 514/44; 514/1; 536/22.1; 435/6; 435/7.1; 435/7.2
(58) Field of Search .................... 514/1, 44; 536/22.1; 435/6, 7.1, 7.2

(56) References Cited

U.S. PATENT DOCUMENTS

| | | | |
|---|---|---|---|
| 3,687,808 | 8/1972 | Merigan et al. ................ 195/28 |
| 4,469,863 | 9/1984 | Ts's et al. ..................... 536/27 |
| 4,476,301 | 10/1984 | Imbach et al. ................ 536/27 |
| 4,587,044 | 5/1986 | Miller et al. .................. 530/211 |
| 4,605,735 | 8/1986 | Miyoshi et al. ............... 536/27 |
| 4,667,025 | 5/1987 | Miyoshi et al. ............... 536/27 |
| 4,762,779 | 8/1988 | Snitman ....................... 435/6 |
| 4,789,737 | 12/1988 | Miyoshi et al. ............... 536/27 |
| 4,824,941 | 4/1989 | Gordon et al. ................ 530/403 |
| 4,828,979 | 5/1989 | Klevan et al. ................ 435/6 |
| 4,835,263 | 5/1989 | Nguyen et al. ............... 536/27 |
| 4,845,205 | 7/1989 | Huynh Dinh et al. ......... 536/28 |
| 4,876,335 | 10/1989 | Yamane et al. ............... 536/27 |
| 4,904,582 | 2/1990 | Tullis .......................... 435/6 |
| 4,948,882 | 8/1990 | Ruth ........................... 536/27 |
| 4,958,013 | 9/1990 | Letsinger .................... 536/27 |
| 4,981,957 | 1/1991 | Lebleu et al. ................ 536/27 |
| 5,023,243 | 6/1991 | Tullis .......................... 514/44 |
| 5,034,506 | 7/1991 | Summerton et al. ......... 528/391 |
| 5,082,830 | 1/1992 | Brakel et al. ................ 514/44 |
| 5,109,124 | 4/1992 | Ramachandran et al. .... 536/27 |
| 5,112,963 | 5/1992 | Pieles et al. ................. 536/27 |
| 5,118,800 | 6/1992 | Smith et al. ................. 536/23 |
| 5,118,802 | 6/1992 | Smith et al. ................. 536/27 |
| 5,130,302 | 7/1992 | Spielvogel et al. .......... 514/45 |
| 5,134,066 | 7/1992 | Rogers et al. ................ 435/91 |
| 5,138,045 | 8/1992 | Cook et al. .................. 536/27 |
| 5,166,315 | 11/1992 | Summerton et al. ......... 528/406 |
| 5,175,273 | 12/1992 | Bischofberger et al. ..... 536/27 |
| 5,177,196 | 1/1993 | Meyer, Jr. et al. ........... 536/22.1 |
| 5,185,444 | 2/1993 | Summerton et al. ......... 544/81 |
| 5,188,897 | 2/1993 | Suhadolnik et al. ......... 428/402.2 |
| 5,214,134 | 5/1993 | Weis et al. ................... 536/25.3 |
| 5,214,136 | 5/1993 | Lin et al. ..................... 514/44 |
| 5,216,141 | 6/1993 | Benner ........................ 536/27.13 |
| 5,218,105 | 6/1993 | Cook et al. .................. 536/25.31 |
| 5,235,033 | 8/1993 | Summerton et al. ......... 528/391 |
| 5,245,022 | 9/1993 | Weis et al. ................... 536/24.5 |
| 5,254,469 | 10/1993 | Warren, II et al. ........... 435/188 |
| 5,258,506 | 11/1993 | Urdea ......................... 536/23.1 |
| 5,262,536 | 11/1993 | Hobbs, Jr. ................... 546/25 |
| 5,264,423 | 11/1993 | Cohen et al. ................ 514/44 |
| 5,264,465 | 11/1993 | Matteucci .................... 536/23.1 |
| 5,264,562 | 11/1993 | Matteucci .................... 536/23.1 |
| 5,272,250 | 12/1993 | Spielvogel et al. .......... 530/300 |
| 5,276,019 | 1/1994 | Cohen et al. ................ 514/44 |
| 5,278,302 | 1/1994 | Caruthers et al. ............ 536/24.5 |
| 5,286,717 | 2/1994 | Cohen et al. ................ 514/44 |
| 5,292,873 | 3/1994 | Rokita et al. ................ 536/24.3 |
| 5,317,098 | 5/1994 | Shizuya et al. .............. 536/23.1 |
| 5,319,080 | 6/1994 | Leumann ..................... 536/27.1 |
| 5,321,131 | 6/1994 | Agrawal et al. ............. 536/25.34 |
| 5,359,044 | 10/1994 | Cook et al. .................. 536/23.1 |
| 5,367,066 | 11/1994 | Urdea et al. ................. 536/24.3 |
| 5,371,241 | 12/1994 | Brush et al. ................. 549/220 |
| 5,391,723 | 2/1995 | Priest .......................... 536/23.1 |
| 5,393,878 | 2/1995 | Leumann ..................... 536/28.2 |
| 5,399,676 | 3/1995 | Froehler ...................... 536/23.1 |
| 5,405,938 | 4/1995 | Summerton et al. ......... 528/406 |
| 5,405,939 | 4/1995 | Suhadolnik et al. ......... 530/322 |
| 5,414,077 | 5/1995 | Lin et al. ..................... 536/24.3 |
| 5,416,203 | 5/1995 | Letsinger .................... 536/25.34 |
| 5,432,272 | 7/1995 | Benner ........................ 536/25.3 |
| 5,433,847 | 7/1995 | Rice ............................ 210/198.2 |
| 5,434,257 | 7/1995 | Matteucci et al. ........... 536/24.3 |
| 5,446,137 | 8/1995 | Maag et al. .................. 536/23.1 |
| 5,451,463 | 9/1995 | Nelson et al. ................ 428/402 |
| 5,453,496 | 9/1995 | Caruthers et al. ............ 536/24.5 |
| 5,455,233 | 10/1995 | Spielvogel et al. .......... 514/44 |
| 5,457,187 | 10/1995 | Gmeiner et al. ............. 536/25.5 |
| 5,459,255 | 10/1995 | Cook et al. .................. 536/27.13 |
| 5,466,677 | 11/1995 | Baxter et al. ................ 514/44 |
| 5,466,786 | 11/1995 | Buhr et al. ................... 536/26.26 |
| 5,470,967 | 11/1995 | Huie et al. ................... 536/24.3 |
| 5,476,925 | 12/1995 | Letsinger et al. ............ 536/23.1 |
| 5,484,908 | 1/1996 | Froehler et al. ............. 536/24.31 |
| 5,486,603 | 1/1996 | Buhr ........................... 536/24.3 |
| 5,489,677 | 2/1996 | Sanghvi et al. .............. 536/22.1 |
| 5,502,177 | 3/1996 | Matteucci et al. ........... 536/260 |
| 5,510,475 | 4/1996 | Agrawal et al. ............. 536/24.3 |
| 5,512,439 | 4/1996 | Hornes et al. ............... 435/6 |
| 5,512,667 | 4/1996 | Reed et al. .................. 536/24.31 |
| 5,514,785 | 5/1996 | Van Ness et al. ............ 536/22.1 |
| 5,519,126 | 5/1996 | Hecht .......................... 536/24.3 |
| 5,519,134 | 5/1996 | Acevedo et al. ............. 544/243 |
| 5,525,465 | 6/1996 | Haralambidis et al. ...... 435/6 |
| 5,525,711 | 6/1996 | Hawkins et al. ............. 536/22.1 |
| 5,536,821 | 7/1996 | Agrawal et al. ............. 536/22.1 |

(List continued on next page.)

Primary Examiner—Jezia Riley
(74) Attorney, Agent, or Firm—Woodcock Washburn Kurtz Mackiewicz & Norris LLP

(57) ABSTRACT

The present invention provides improved methods for tracking the biodistribution of macromolecules and carriers in cells. In accordance with one embodiment, oligonucleotides and lipid carriers are differentially fluorescently labeled and coadministered to the cells. Useful compounds and synthetic methods are also provided.

27 Claims, No Drawings

U.S. PATENT DOCUMENTS

| | | | |
|---|---|---|---|
| 5,539,082 | 7/1996 | Nielsen et al. | 530/300 |
| 5,541,306 | 7/1996 | Agrawal et al. | 536/22.1 |
| 5,541,307 | 7/1996 | Cook et al. | 536/23.1 |
| 5,541,313 | 7/1996 | Ruth | 536/24.3 |
| 5,545,730 | 8/1996 | Urdea et al. | 536/28.51 |
| 5,550,111 | 8/1996 | Suhadolnik et al. | 514/44 |
| 5,552,538 | 9/1996 | Urdea et al. | 536/24.3 |
| 5,552,540 | 9/1996 | Haralambidis | 536/25.34 |
| 5,561,225 | 10/1996 | Maddry et al. | 536/23.1 |
| 5,563,033 * | 10/1996 | Lawrence et al. | 435/6 |
| 5,563,253 | 10/1996 | Agrawal et al. | 536/22.1 |
| 5,565,552 | 10/1996 | Magda et al. | 534/11 |
| 5,567,810 | 10/1996 | Weis et al. | 536/25.3 |
| 5,567,811 | 10/1996 | Misiura et al. | 536/25.34 |
| 5,571,799 | 11/1996 | Tkachuk et al. | 514/47 |
| 5,574,142 | 11/1996 | Meyer, Jr. et al. | 536/23.1 |
| 5,576,427 | 11/1996 | Cook et al. | 536/23.1 |
| 5,578,717 | 11/1996 | Urdea et al. | 536/26.1 |
| 5,578,718 | 11/1996 | Cook et al. | 536/27.21 |
| 5,580,731 | 12/1996 | Chang et al. | 435/6 |
| 5,585,481 | 12/1996 | Arnold, Jr. et al. | 536/25.33 |
| 5,587,361 | 12/1996 | Cook et al. | 514/44 |
| 5,587,371 | 12/1996 | Sessler et al. | 514/185 |
| 5,587,469 | 12/1996 | Cook et al. | 536/23.1 |
| 5,591,584 | 1/1997 | Chang et al. | 435/6 |
| 5,591,722 | 1/1997 | Montgomery et al. | 514/45 |
| 5,594,121 | 1/1997 | Froehler et al. | 536/23.5 |
| 5,595,726 | 1/1997 | Magda et al. | 424/9.61 |
| 5,596,086 | 1/1997 | Matteucci et al. | 536/22.1 |
| 5,596,091 | 1/1997 | Switzer | 536/24.5 |
| 5,597,696 | 1/1997 | Linn et al. | 435/6 |
| 5,597,909 | 1/1997 | Urdea et al. | 536/24.3 |
| 5,599,923 | 2/1997 | Sessler et al. | 540/145 |
| 5,599,928 | 2/1997 | Hammi et al. | 540/474 |
| 5,602,240 | 2/1997 | De Mesmaeker et al. | 536/23.1 |
| 5,608,046 | 3/1997 | Cook et al. | 536/23.1 |
| 5,610,289 | 3/1997 | Cook et al. | 536/25.34 |
| 5,610,300 | 3/1997 | Altmann et al. | 544/244 |
| 5,614,617 | 3/1997 | Cook et al. | 536/23.1 |
| 5,618,704 | 4/1997 | Sanghvi et al. | 435/91.5 |
| 5,623,070 | 4/1997 | Cook et al. | 536/27.6 |
| 5,625,050 | 4/1997 | Beaton et al. | 536/24.1 |
| 5,627,053 | 5/1997 | Usman et al. | 435/91.1 |
| 5,633,360 | 5/1997 | Bischofberger et al. | 536/22.1 |
| 5,639,873 | 6/1997 | Barascut et al. | 536/25.3 |
| 5,646,265 | 7/1997 | McGee | 536/25.34 |
| 5,658,873 | 8/1997 | Bertsch-Frank et al. | 510/375 |
| 5,663,312 | 9/1997 | Chaturvedula | 536/22.1 |
| 5,670,633 | 9/1997 | Cook et al. | 536/23.1 |
| 5,677,437 | 10/1997 | Teng et al. | 536/23.1 |
| 5,677,439 | 10/1997 | Weis et al. | 536/23.1 |
| 5,681,941 | 10/1997 | Cook et al. | 536/23.1 |
| 5,688,941 | 11/1997 | Cook et al. | 536/25.3 |
| 5,697,248 | 12/1997 | Brown et al. | 73/290 |
| 5,700,920 | 12/1997 | Altmann et al. | 536/221 |
| 5,714,331 | 2/1998 | Buchardt et al. | 435/6 |
| 5,719,262 | 2/1998 | Buchardt et al. | 530/300 |
| 5,837,283 * | 11/1998 | McDonald et al. | 424/450 |

* cited by examiner

METHODS AND COMPOUNDS FOR TRACKING THE BIODISTRIBUTION OF MACROMOLECULE-CARRIER COMBINATIONS

FIELD OF THE INVENTION

This invention relates to the use of fluorescently labeled carriers and macromolecules for following cellular trafficking of certain macromolecule-carrier combinations. In particular embodiments, this invention can be utilized to determine cellular pathways for oligonucleotide uptake and to ascertain biodistribution of macromolecules and carriers in cells.

BACKGROUND OF THE INVENTION

Antisense oligonucleotides specifically target a messenger RNA. They have found a wide range of in vitro functions including roles in diagnostics and research. They are also a potentially important class of novel therapeutics, with several in clinical trials.

In order to find its target in vitro, an oligonucleotide must enter the cell and localize to its target in the cytoplasm and/or nucleus. Unmodified oligonucleotides have demonstrated poor ability to cross cell membranes. Several approaches to enhance the uptake of oligonucleotides have been tried, including liposomal encapsulation, conjugation with other ligands, such as cholesterol, peptides and polylysines, and cationic lipids. Cationic lipids have been shown to increase the cellular uptake of oligonucleotides, but the mechanism by which this occurs is not well understood (Bennett, C. F., et al., *Mol. Pharmacol.* 1992 41, 1023–1033).

Oligonucleotide uptake is thought to proceed initially by interaction with cell surface proteins, followed by internalization through an endocytic mechanism (Loke, S. L., et al., *Proc. Natl. Acad. Sci. USA* 1989, 86, 3474–3478). These events lead to a punctate distribution of the oligonucleotides in intracellullar membrane-bound structures, which are thought to represent endosomes and lysosomes (Bennett, C. F., et al., *Mol. Pharmacol.* 1992, 41, 1023–1033). The sequestration of oligonucleotides into endosomal compartments may prevent their interaction with their target mRNA and hence decrease their activity.

One of the most commonly used enhancers is a mixture of a neutral lipid with a cationic lipid. The cationic lipid is thought to be the more crucial part of this mixture, as cationic lipids increase the activity of antisense oligonucleotides, whereas neutral lipids cannot. The mechanism by which cationic lipids increase the activity of antisense oligonucleotides is poorly understood. It was recently demonstrated that oligonucleotide-lipid complexes are taken into the cell via an endocytic mechanism and do not simply fuse with the plasma membrane (Zelphati, O. and Szoka, F. C., Jr., *Pharmacol. Res.* 1996, 13, 1367–1372). It is also known that cationic lipids enhance cellular accumulation of the oligonucleotide by increasing the amount that escapes from the endosomal pathway and thus has an opportunity to interact with its target mRNA (Bennett, C. F., et al., *Mol. Pharmacol.* 1992, 41, 1023–1033). While the mechanism by which an oligonucleotide is released from the endocytic compartments in order to gain access to its RNA target is not well characterized, models have been proposed (Zelphati, O. and Szoka, F. C., Jr., *Proc. Natl. Acad. Sci. USA* 1996, 93, 11493–11498). Fluorescence studies by Zelphati, O. and Szoka, F. C., Jr. have recently shown that when transfected with a cationic/neutral lipid mixture, oligonucleotides reached the nucleus while the neutral lipid stayed in punctate structures within the cytoplasm. These punctate structures were presumed to be endosome. However, the final destination of the cationic lipid was not examined in this study and whether the cationic lipid traffics together with the oligonucleotide to the nucleus was not determined.

Fully understanding the mechanism by which oligonucleotides are taken up by cells and released from endosomes will aid in the design of delivery vehicles to improve both in vitro and in vivo efficacy. Such improved designs are important in the investigation of the therapeutic utility of antisense oligonucleotides and to improve the dosing regimens for antisense therapeutics.

In Zelphati, O. and Szoka, F. C., Jr., cationic lipids were labeled with rhodamine and oligonucleotides were labeled with fluorescein. The mixture was introduced to cells. However, it is known that fluorescein has a quenching effect with respect to the cell culture medium, which results in loss of the fluorescent signal. Quenching also occurs using fluoroscein in acidic cellular environments, including endosomes, lysosomes and lipophilic cell surfaces. With quenching, it becomes more difficult to follow macromolecules, especially oligonucleotides, to such environments.

Thus, there remains a need for improved methods for tracking the distribution of carriers and macromolecules within a cell.

BRIEF DESCRIPTION OF THE INVENTION

In accordance with this invention there are provided methods of tracking the cellular trafficking of a macromolecule and a carrier in a cell, especially in appropriate cell culture medium comprising selecting a macromolecule with a first label and a carrier with a second label. The second label is selected to be distinguishable from the first label and both of the first and second labels are substantially free from quenching effects with respect to said cell culture medium and acidic cellular environments. The macromolecule labeled with said first fluorescent label and the carrier labeled with said second fluorescent label are then coadministered to the cell and the labels are tracked to distinguish each of said labels within the cell.

Also provided are compounds useful for carrying out the methods of the invention. Preferred from among such compounds are those have the general formula:

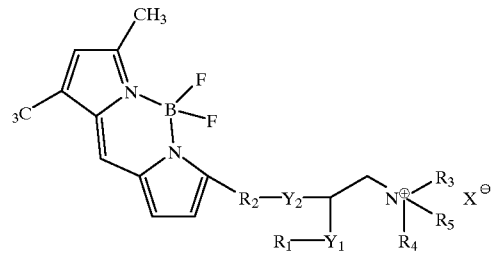

Wherein $R_1$ is preferably an aliphatic group having from 12 to about 20 carbon atoms or a steroid molecule while $R_2$ is preferably an aliphatic group having from 12 to about 20 carbon atoms. $R_3$ and $R_4$ are preferably $CH_3$ or $CH_2CH_3$ while $R_5$ is preferred to be $CH_3$, $(CH_2)_n CH_3$ where n=1 or 2, or $(CH_2)_n OH$ where n=1 to 5. The value of X is preferably Br, I, or Cl and Y, and $Y_2$ are, independently, an ether, an ester, a carbamate, a carbonate, an amide, a peptide linkage, or a urea linkage.

In accordance with other preferred embodiments, compounds of the structure:

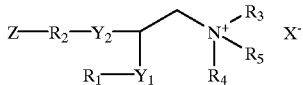

are provided for use with the methods of the present invention wherein the values for $R_1$, $R_2$, $R_3$, $R_4$, $R_5$, $Y_1$, $Y_2$ and X are as set forth above and Z is a label, preferably a fluorescent label.

DETAILED DESCRIPTION OF PREFERRED EMBODIMENTS

The methods and compounds of the invention provide improved means to measure the cellular trafficking of a macromolecule and a carrier. A macromolecule is a molecule of interest that is desired to be introduced to the cell. A carrier is the delivery vehicle for that macromolecule. It is desirable to understand and determine the cellular trafficking of such a complex. This will allow further improvements in the design of these macromolecules and carriers.

A macromolecule as used in this invention includes polynucleotides, including DNA, RNA and oligonucleotides, proteins or peptides, and antibodies. These macromolecules may have therapeutic potential as in the case of antisense oligonucleotides, ribozymes, bioactive peptides, and monoclonal antibodies. In preferred embodiments of the invention, the macromolecule is an antisense oligonucleotide.

Carriers as that term is used in this invention, include anything capable of enhancing the delivery of a macromolecule into a cell and to its final destination within a cell. This would include cationic lipids (Bennett, C. F., et al., *Mol. Pharmacol.* 1992, 41, 1023–1033), liposomes (Bennett, C. F., *Delivery Strategies for Antisense Oligonucleotide Therapeutics*, Akhtar, S. (ed.) CRC Press, Boca Raton, Fla., 1995, pp. 223–232), peptides (Bongartz, J. P., et al., *Nucleic Acids Res.* 1994, 22, 4681–4688), polycations (Boussif, O., et al., *Proc. Natl. Acad. Sci. USA* 1995, 92, 7297–7301), dendrimers (Bielinska, A., et al., *Nucl. Acids Res.* 1996, 24, 2176–2182) and conjugation with cholesterol (Krieg, A. M., et al., *Proc. Natl. Acad. Sci. USA* 1993, 90, 1048–1052).

In a preferred embodiment of the invention, cationic lipids are used as a delivery vehicle. Since this delivery mechanism is based on electrostatic interactions between a negatively charged oligonucleotide and a positively charged cationic lipid, encapsulation is not required (Zelphati, O. and Szoka, F. C., Jr., *J. Controlled Release* 1996, 41, 99–119). A direct mixing is sufficient to provide completely coverage of the oligonucleotide. Some commonly used cationic lipids are disclosed in Zelphati, O. and Szoka, F. C., Jr. (*J. Controlled Release* 1996, 41, 99–119). These include N-(1-(2,3-dioleoyloxy)propyl)-N,N,N-trimethyl ammonium chloride (DOTMA); 1,2-dioleoyl-3-trimethylammonium-propane (DOTAP); dimethyldioctdecylammonium bromide (DDAB); dioctdecylamidoglycyl spermine (DOGS); and 1,2-dioleoyl-sn-glycero-3-phosphoethanolamine (DOPE). In addition, a steroid molecule, such as cholesterol, can be used as a helper.

A general structure for preferred cationic lipids in accordance with this invention is shown in the formula:

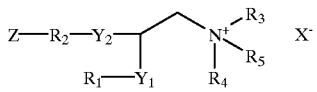

The side chains $R_1$ and $R_2$ may include aliphatic groups such as alkyl or substituted alkyl, alkenyl or substituted alkenyl, alkynyl or substituted alkynyl. Preferably, the alkyl, alkenyl and alkynyl substituent groups have from 12 to about 20 carbons. The side chains may also include a steroid molecule. A preferred steroid is cholesterol. A cholesterol side chain on a cationic lipid is disclosed by Ledley, F. D. (*Curr. Opin. Biotech.* 1994, 5, 626–636).

X is preferably a halogen selected from Br, Cl, and I, especially Br and Cl and most especially Br. $Y_1$ and $Y_2$ are linkages and can be of the types: ether —O— or —S—; ester —C(O)—O— or —C(O)—S—; peptide, carbamate —O—C(O)—N— or —S—C(O)—N—; carbonate 13 O—C(O)—O— or —S—C(O)—S—; amide —C(O)—N; or urea —N—C(O)—N—. $R_3$ and $R_4$ can preferably be $CH_3$ or $CH_2CH_3$ while $R_5$ is preferably $CH_3$, $(CH_2)_nCH_3$, where n=1 or 2, and $(CH_2)_nOH$ where n is an integer from 1 to 5.

Some representative cationic lipid structures are disclosed in Bennett, C. F., et al. (*J. Drug Targeting* 1997, 5, 149–162)

The macromolecules and carriers are preferably fluorescently labeled. Such labels are unique from each other, readily distinguishable from each other, and can be selected to be free from quenching effects with respect to the cell culture medium and acidic cellular environments.

Exemplary fluorescent labels that can be used on the macromolecule or carrier include CY3™ and CY5™ (succinimidyl esters available from Amersham Pharmacia Biotech, Piscataway, N.J.), rhodamine, Texas Red® (Molecular Probes, Inc. of Eugene, Oreg.). Other labels may be used so long as they free from quenching effects with respect to the cell culture medium and acidic cellular environments. In selecting a pair of labels, it is important that they are readily distinguishable from each other. A preferred label for a cationic lipid carrier is BODIPY® (4,4-difluoro-3a,4a-diaza-s-indacene) available from Molecular Probes (Eugene, Oreg.). A single BODIPY® molecule can be incorporated into one side chain of the cationic lipid of general formula [II]. The preferred label for the macromolecule, when using BODIPY® on the carrier, is rhodamine.

The manner of making the fluorescently labeled cationic lipids of this invention is preferably through a novel process. Fluorescently labeled cationic lipids are not commonly made due to the difficulty in obtaining the pure, desired product. Multiple side reactions occur when a fluorescent dye is reacted with a cationic lipid. Some of these products are also fluorescent, making the isolation of the desired product difficult. Also, yields are low. In accordance with this invention, a fluorescent dye is reacted with a cationic lipid under anhydrous conditions and subsequently, the desired product is preferably isolated using radial chromatography as described in U.S. Pat. No. 5,433,847, herein incorporated by reference.

Coadministrating, in the context of this invention, may include direct mixing of lipid and oligonucleotide (cationic lipids), encapsulation of oligonucleotide within a lipid (neutral lipids), and conjugation of the carrier to the oligonucleotide (cholesterol). In any event, coadministering means the effectively simultaneous delivery of macromolecule and carrier.

Cell culture medium is a growth medium capable of supporting a cell line. Recommendations for cell culture media are frequently provided by the supplier (e.g. American Type Culture Collection, Manassas, Va.) or are available in the published literature. Any culture medium effective for growth or maintenance of cells to be evaluated may be used.

Tracking the biodistribution of the macromolecule and carrier can be accomplished by any technique or instrument that can visualize or isolate cellular structures and detect fluorescent signals. A preferred embodiment of this invention is the use of confocal fluorescent microscopy.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. No. 5,539,082; 5,714,331; and 5,719,262. Further teaching of PNA compounds can be found in Nielsen et al. (*Science,* 1991, 254, 1497–1500).

Most preferred embodiments of the invention are oligonucleotides with phosphorothioate backbones and oligonucleosides with heteroatom backbones, and in particular $-CH_2-NH-O-CH_2-$, $-CH_2-N(CH_3)-O-CH_2-$ [known as a methylene (methylimino) or MMI backbone], $-CH_2-O-N(CH_3)-CH_2-$, $-CH_2-N(CH_3)-N(CH_3)-CH_2-$ and $-O-N(CH_3)-CH_2-CH_2-$ [wherein the native phosphodiester backbone is represented as $-O-P-O-CH_2-$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl, O-alkyl-O-alkyl, O-, S-, or N-alkenyl, or O-, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_2ON(CH_3)_2$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O-$CH_2CH_2OCH_3$, also known as 2'-O-(2-methoxyethyl) or 2'-MOE) (Martin et al., Helv. Chim. Acta 1995, 78, 486–504) i.e., an alkoxyalkoxy group.

Other preferred modifications include 2'-methoxy (2'-O-$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the Concise Encyclopedia Of Polymer Science And Engineering 1990, pages 858–859, Kroschwitz, J. I., ed. John Wiley & Sons, those disclosed by Englisch et al. (Angewandte Chemie, International Edition 1991, 30, 613–722), and those disclosed by Sanghvi, Y. S., Chapter 15, Antisense Research and Applications 1993, pages 289–302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyl-adenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., Antisense Research and Applications 1993, CRC Press, Boca Raton, pages 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA 1989, 86, 6553–6556), cholic acid (Manoharan et al., Bioorg. Med. Chem. Lett. 1994, 4, 1053–1059), a thioether, e.g., hexyl-S-tritylthiol (Manoharan et al., Ann. N.Y. Acad. Sci. 1992, 660, 306–309; Manoharan et al., Bioorg. Med. Chem. Let. 1993, 3, 2765–2770), a thiocholesterol (Oberhauser et al., Nucl. Acids Res. 1992, 20, 533–538), an aliphatic chain, e.g., dodecandiol or undecyl residues (Saison-Behmoaras et al., EMBO J. 1991, 10, 1111–1118; Kabanov et al., FEBS Lett. 1990, 259, 327–330; Svinarchuk et al., Biochimie 1993, 75, 49–54), a phospholipid, e.g., di-hexadecyl-rac-glycerol or triethylammonium 1,2-di-O-hexadecyl-rac-glycero-3-H-phosphonate (Manoharan et al., Tetrahedron Lett. 1995, 36, 3651–3654; Shea et al., Nucl. Acids Res. 1990, 18, 3777–3783), a polyamine or a polyethylene glycol chain (Manoharan et al., Nucleosides & Nucleotides 1995, 14, 969–973), or adamantane acetic acid (Manoharan et al., Tetrahedron Lett. 1995, 36, 3651–3654), a palmityl moiety (Mishra et al., Biochim. Biophys. Acta 1995, 1264, 229–237), or an octadecylamine or hexylamino-carbonyl-oxycholesterol moiety (Crooke et al., J. Pharmacol. Exp. Ther. 1996, 277, 923–937).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., 2'-fluoro- or 2'-O-methoxyethyl-substituted). Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa.

In one embodiment, the oligonucleotides of the present invention contain a 2'-O-methoxyethyl (2'-O—$CH_2CH_2OCH_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—$CH_2CH_2OCH_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred.

EXAMPLES

Examples 1–6 are depicted in Scheme 1. The underlined numbers in parentheses following the Example's title compound correspond to the compound numbers in Scheme 1. Syntheses are preferably performed anhydrously.

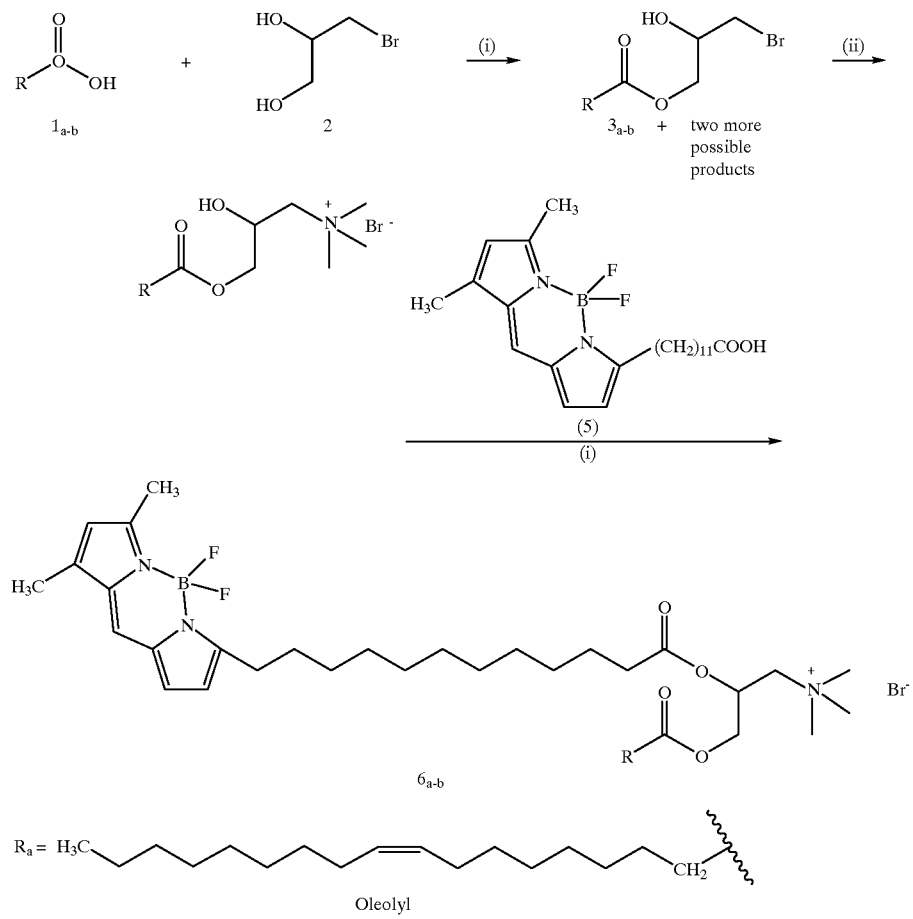

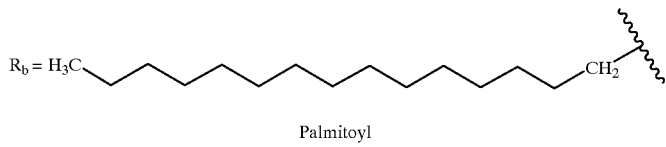

Palmitoyl (i) 1-(3-Dimethylaminopropyl)-3-ethylcarbodiimide hydrochloride/DMAP/CH$_2$Cl$_2$ room temperature, overnight
(ii) trimethyl amine/toluene/60° C., overnight.

Example 1

Synthesis of 1-O-Oleolyl-2-Hydroxy-3-bromopropane (3a)

A solution of oleic acid (5.0 gm, 17.7 mmol), EDC (3.75 gm, 19.6 mmol) (Advanced Chemtech, Louisville, Ky.) and DMAP (0.24 gm, 1.9 mmol) (Aldrich, Milwaukee, Wis.) in anhydrous CH$_2$Cl$_2$ (200 ml) was stirred at room temperature for 30 min and to this was then added 3-bromo-1,2-propane diol (3.03 gm, 19.5 mmol). The reaction mixture was stirred overnight when the tlc system (15% EtOAc/hexane) indicated that the reaction was complete. It was washed with water (3×50 ml), dried over anhydrous Na$_2$SO$_4$ and the solvent removed under reduced pressure. The residual oil was purified by column chromatography using 10–20% EtOAc in hexane as the eluant. The appropriate fractions were concentrated containing the mixture of monoacylated products were concentrated and dried to give an oil yield= 3.4 gm, 61%, $^1$H NMR (CDCl$_3$): d 5.37–5.31 (m, 2H), 4.21 (d, 2H, J=4.9 Hz), 4.14–43.95 (m, 1H), 3.85 (bs, 1H), 3.55–3.40 (m, 2H), 2.40–2.31 (m, 2H), 2.10–1.92 (m, 4H), 1.75–1.55 (m, 2H), 1.40–1.20 (m, 20H), 0.90–0.84 (bt, 3H).

Example 2

Synthesis of 1-O-Palmitoyl-2-Hydroxy-3-bromopropane (3b)

A solution of palmitic acid (4.6 gm, 17.7 mmol), EDC (3.75 gm, 19.6 mmol) (Advanced Chemtech, Louisville, Ky.) and DMAP (0.24 gm, 1.9 mmol) (Aldrich, Milwaukee, Wis.) in anhydrous CH$_2$Cl$_2$ (200 ml) was stirred at room temperature for 30 min and to this was then added 3-bromo-1,2-propane diol (3.03 gm, 19.5 mmol). The reaction mixture was stirred overnight when the tlc system (15% EtOAc/hexane) indicated that the reaction was complete. It was washed with water (3×50 ml), dried over anhydrous Na$_2$SO$_4$ and the solvent removed under reduced pressure. The residual oil was purified by column chromatography using 10–20% EtOAc in hexane as the eluant. The appropriate fractions were concentrated containing the mixture of monoacylated products were concentrated and dried to give an oil yield=2.9 gm, in 56% yield, $^1$H NMR (CDCl$_3$):d 4.23 (d, 2H), 4.05 (m, 1H), 3.5 (m, 2H), 2.35 (t, 2H), 1.64 (d, 2H), 1.3 (s, 24H), 0.86 (t, 3H).

Example 3

Synthesis of 1-O-Oleolyl-2-hydroxy-NNN-trimethyl-3-aminopropane bromide (4a)

A mixture of monosubstituted ester derivatives 3a (3.0 gm) was dissolved in anhydrous toluene (20 ml) and it was added to anhydrous trimethylamine (5 ml) cooled to −78° C. in a pressure bottle. The pressure vessel was sealed and then heated at 60° C. bath temperature, overnight. The solution was cooled and then the contents were transferred to a round bottomed flask. The solvent was removed under reduced pressure and the residue triturated with ether (30 ml) and the ether was decanted off. The residual oil was dried under vacuum to furnish the desired compound as an oil. yield=2.0 gm, 58%, $^1$H NMR (CDCl$_3$): d 5.35–5.26 (m, 2H), 4.65 (bs, 1H), 4.27–4.08 (m, 2H), 3.70–3.62 (m, 2H), 3.49 (bs, 9H), 2.89 (bs 1H), 2.41–2.31 (m, 2H) 2.08–1.90 (m, 4H), 1.65–1.50 (m, 2H), 1.26 (bs, 20H), 0.85 (bt, 3H); ESMS (MH+ive) 399.2.

Example 4

Synthesis of 1-palmitoyl-2-hydroxy-NNN-trimethyl-3-aminopropane bromide (4b)

A mixture of monosubstituted palmitic ester derivatives 3b (3.0 gm) was dissolved in anhydrous toluene (20 ml) and it was added to anhydrous trimethylamine (5 ml) cooled to −78° C. in a pressure bottle. The pressure vessel was sealed and then heated at 60° C. bath temperature, overnight. The solution was cooled and then the contents were transferred to a round bottomed flask. The solvent was removed under reduced pressure and the residue triturated with ether (30 ml) and the ether was decanted off. The residual oil was dried under vacuum to furnish the desired compound as an oil. yield 40%, $^1$H NMR (CDCl$_3$): d 4.68 (m, 1H) 4.18 (m, 2H), 3.70 (d, 2H), 3.50 (s, 9H), 2.37 (t, 2H), 1.60 (bs, 2H), 1.30 (s, 24H), 0.87 (t, 3H).

Example 5

Synthesis of 1-O-Oleolyl-2-([BODIPY®]-dodecanoyl)-N,N,N-trimethyl-3-aminopropane bromide (6a)

A solution of BODIPY®-dodecanoic acid (5.0 mg, 0.011 mmol), EDC (5.0 mg, 0.026 mmol) and DMAP (2.0 mg, 0.016 mmol) in anhydrous CH$_2$Cl$_2$ (1 ml) was stirred for 15 minutes and to this solution was added compound 4a (15 mg, 0.031 mmol) and the reaction mixture was allowed to stir overnight at room temperature. The solvent was removed and the product was purified by radial chromatography using 10–20% MeOH in CH$_2$Cl$_2$ saturated with H$_2$O (~3–4%) as the eluant. The appropriate fractions were concentrated to give the desired compound as a highly fluorescent greenish yellow compound, yield=2.5 mg, 25%. ESMS: M+=799.1 (All manipulations were carried out in the dark)

Example 6

Synthesis of 1-O-Palmitoyl-2-([BODIPY®]-dodecanoyl)-N,N,N-trimethyl-3-aminopropane chloride (6b)

A solution of BODIPY®-dodecanoic acid (5.0 mg, 0.011 mmol), EDC (5.0 mg, 0.026 mmol) and DMAP (2.0 mg, 0.016 mmol) in anhydrous CH$_2$Cl$_2$ (1 ml) was stirred for 15 minutes and to this solution was added palmitic acid derivative 4b (15 mg, 0.031 mmol) and the reaction mixture was allowed to stir overnight at room temperature. The solvent was removed and the product was purified by radial chromatography using 10–20% MeOH in CH$_2$Cl$_2$ saturated with H$_2$O (3–4%) as the eluant. Purification was done as described in Example 5, except the plate was washed with dilute HCl (pH=3). The appropriate fractions were concentrated to give the desired compound as a highly fluorescent greenish yellow compound yield=22%. ESMS: M+=773.0

Example 7
Preparation of lipid mixtures

All lipids were dissolved in chloroform. The appropriate amounts of lipids were then added to glass vials and dried under argon. The vials were left under vacuum overnight to ensure that all traces of the chloroform were removed. The vials were capped and stored in the dark at −20° C. On the day of the experiment the vials were removed and the lipids rehydrated in water at a concentration of between 0.5 and 2 mg/ml. The lipids were sonicated in an inverted cup sonicator and then passed three times through an extruder with a 200 nm pore size filter in order to ensure uniformity of particle size.

Example 8
Synthesis of ISIS 3521 with an aminolinker

Phosphorothioate oligodeoxynucleotides are synthesized on an automated DNA synthesizer (Applied Biosystems model 380B) using standard phosphoramidite chemistry with the standard oxidation bottle was replaced by a 0.2 M solution of $^3$H-1,2 -benzodithiole-3-one 1,1-dioxide in acetonitrile for the stepwise thiation of the phosphite linkages. β-cyanoethyldiisopropyl-phosphoramidites are purchased from Applied Biosystems (Foster City, Calif.). The thiation cycle wait step was increased to 68 seconds and was followed by the capping step. At the 5′-end an aminolinker was coupled (5′-Amino-Modifier C6, Glen Research, Sterling, Va.) from a 0.2 M solution in acetonitrile. The oxidation was done as a regular synthetic step. The monomethoxytrityl group was removed in the machine by repeated detritylation steps.

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were checked by $^{31}$P nuclear magnetic resonance spectroscopy.

The sequence of ISIS 3521 is:
5′-GTTCTCGCTGGTGAGTTTCA-3′ (SEQ ID NO. 1)
This oligonucleotide targets human PKC-a mRNA.

Example 9
Synthesis of ISIS 3521-Rhodamine Conjugate:

10 OD units of oligonucleotide with the aminolinker was evaporated and redissolved in 1M $Na_2CO_3$/$NaHCO_3$ (pH 9.0; 100 microliters). To this solution a solution of 5 mg tetramethylrhodamine isothiocyanate in 100 microliters of DMF (Molecular Probes, Eugene, Oreg.) was added. The solution was covered with aluminum foil and left overnight. Then it was passed through a Sephadex G-25 column and the first eluent was collected and purified by reverse phase HPLC. (Waters 600E HPLC system with a 991 detector using a Waters C4 Prep. scale column and the following solvents: A: 50 mM TEA-Ac, pH 7.0 and B: acetonitrile utilizing the "MPREP2" method). The purified conjugate was further analyzed by CE and mass spectral analysis.

Example 10
Northern blot assays of A549 cells treated with lipid mixtures

A549 cells (lung carcinoma) were obtained from the American Type Culture Collection (ATCC, Manassas, Va.). The cells were grown in 75 cm$^2$ flasks in DME (Gibco/BRL, Bethesda, Md.), 10% fetal bovine serum (FBS; Irvine Scientific, Irvine, Calif.) until they reached 75% confluency. The cells were then washed once in OPTI-MEM® (Gibco/BRL) and treated with 5 ml OPTI-MEM® containing the indicated concentrations of a 1:1 mixture of DOPE and DOTAP (5% of which was the BODIPY® derivative of DOTAP of example 5) and oligonucleotide. The cells were then incubated at 37° C. for the indicated time before being washed once with cold phosphate-buffered saline (PBS) and harvested in 3.5 ml guanidinium isothiocyanate. The harvested solution was then passed twice through an 18 gauge needle before being layered on top of 1.5 ml 5.7 M CsCl and centrifuged at 30,000 rpm in a SW55 rotor for 14–20 hr. The pellet was resuspended and ethanol precipitated twice. The RNA was quanitiated by spectrophotometer and 15 mg was resolved on a 1% agarose-formaldehyde gel. The gel contents were transferred to a nylon membrane and the blot prehybridized with QUIKHYB® (Stratagene, La Jolla, Calif.) before being probed with $^{32}$P-labeled fragments that hybridize to the coding region of PKC-a or glyceraldehyde 3-phosphate dehydrogenase (G3PDH). The bands were quantitated on a phophorimager (Molecular Dynamics, Sunnyvale, Calif.) and the PKC-a mRNA levels normalized to the G3PDH mRNA levels.

Example 11
Fluorescence microscopy of A549 cells treated with lipid mixtures A549 cells were grown on plastic 4-chambered slides (Nunc, Nutley, N.J.) until they reached 75% confluency. The cells were then treated with 15 mg/ml 1:1 mixture of DOPE and DOTAP (5% of which was the BODIPY® derivative of DOTAP of example 5) and 300 nM ISIS 3521R. After the indicated times the slides were removed from the 37° C. incubator and washed threee times with DME, 10% FBS and twice with PBS. The cells were then covered and photographed lived with a fluorescence microscope through either a 20× or 40× objective.

Example 12
Dose-dependent reduction of PKC-a mRNA by ISIS 3521R

ISIS 3521R (SEQ ID NO. 3) was tested for its ability to inhibit PKC-a expression in a dose-dependent manner. The oligonucleotide was mixed with lipid mixture and introduced to A549 cells as described in Example 8. Cells were incubated for 4 hrs and the concentrations of oligonucleotide used were 25, 50, 100, 150, 200, 300, and 400 nM. Northern blots were used to quantitate PKC-a mRNA. An $IC_{50}$ of 150 nm was determined, similar to that seen with the unlabeled oligonucleotide ISIS 3521 (SEQ ID NO. 2). Additionally, the use of BODIPY® labeled DOTAP derivative versus unlabeled DOTAP did not affect the efficacy of the oligonucleotide. Thus, the fluorescent labels used did not affect either the oligonucleotide or cationic lipid.

Example 13
Time-course of oligodeoxynucleotide-lipid complex uptake

The labeled molecules were used to study the uptake and biodistribution of these oligonucleotide-cationic lipid complexes. The protocol was as described in Example 9. Slides were examined at 0, 30, 60, 120, and 240 minutes.

At time 0 no cellular fluorescence was detected, demonstrating a lack of background autofluorescence. The cells surface was stained brightly at 30 min by the cationic lipid (green). ISIS 3521R (SEQ ID NO. 3) could also be seen (red), but in a more discrete punctate pattern. After 60 min incubation some of the cationic lipid could still be seen at the cell surface, but a portion had been internalized and could be found in very fine speckles with a pattern reminiscent of the endosomal system. The oligonucleotide could be seen in these same structures, however, in addition, a small percentage of nuclei also contained red fluorescence. By 120 min almost all of the cationic lipid could be seen in the very fine speckles within the cytoplasm, however, no nuclei stained green. In contrast, many more (~50%) of the nuclei were stained red with oligonucleotide at this time. This staining pattern did not change appreciably after an additional 2 hr incubation, except that more nuclei (up to 80%) became positively stained with oligonucleotide. At this time nuclear staining was also much darker, indicating a greater accumulation of the oligonucleotide. At all times there were some larger punctate structures that appeared to contain both cationic lipid and oligonucleotide. These were possibly large aggregates of the oligonucleotide-lipid compex adhered to the cell surface but were not internalized.

Double exposure photographs showed that at both 120 and 240 min incubation a portion of the cationic lipid (green) and oligonucleotide (red) co-localized into cytoplasmic punctate structures (orange). However, a large percentage of the oligonucleotide (red) could be found in the nucleus. Higher magnification photographs also showed the cationic lipid co-localized with a portion of the oligonucleotide in fine speckles and larger punctate cytoplasmic structures, while a large percentage of the oligonucleotide was found in the nucleus. At no time was the cationic lipid localized in the nucleus.

The final destination of the cationic lipid appeared to be in very fine speckles scattered throughout the cytoplasm, which surrounded, but did not include, the nucleus of the cell. This pattern of staining would be anticipated if the cationic lipid remained in endosomal and lysosomal compartments.

What is claimed is:

1. A method for tracking a macromolecule and a carrier in a cell comprising:

providing a macromolecule having a first label;

providing a carrier with a second label, said second label being selected to be distinguishable from said first label, said first and second labels each being fluorescent labels effectively free from quenching effects in the environment of the cell and in acidic environment;

coadministering said macromolecule labeled with said first label and said carrier labeled with said second label to said cell; and tracking said first and second labels to distinguish said labels within the cell.

2. The method of claim 1 wherein the cell is in a cell culture medium and said fluorescent labels are effectively free from quenching effects in said medium.

3. The method of claim 1, wherein said carrier is a cationic lipid.

4. The method of claim 1, wherein said macromolecule is an oligonucleotide.

5. The method of claim 3, wherein said cationic lipid is labeled with 4,4-difluoro-3a,4a-diaza-s-indacene.

6. The method of claim 1 wherein said tracking comprises monitoring the biodistribution of said molecule in the cell.

7. The method of claim 3, wherein said cationic lipid having said second label attached is of formula:

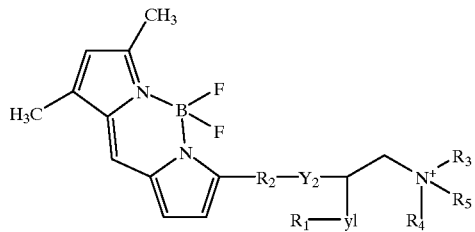

wherein $R_1$ is an aliphatic group having from 12 to about 20 carbon atoms or a steroid molecule;

$R_2$ is an aliphatic group having from 12 to about 20 carbon atoms;

$R_3$, $R_4$ are $CH_3$ or $CH_2CH_3$;

$R_5$ is $CH_3$, $(CH_2)_nCH_3$ where n=1 or 2, or $(CH_2)_nOH$ where n=1 to 5;

X is Br, I, or Cl; and $Y_1$, $Y_2$ are, independently, an ether, an ester, a carbamate, a peptide linkage, a carbonate, an amide, or a urea linkage.

8. The method of claim 7, wherein said macromolecule is an oligonucleotide.

9. The method of claim 7 wherein said first label is rhodamine.

10. The method of claim 7, wherein $R_1$ is cholesterol.

11. The method of claim 7, wherein X is Br.

12. The method of claim 7, wherein $R_3$, $R_4$, and $R_5$ are $CH_3$, and $R_2$ is alkyl.

13. The method of claim 7, wherein $R_1$ is alkyl or alkenyl.

14. The method of claim 7, wherein $R_1$ is a straight chain alkenyl of about 17 carbons.

15. The method of claim 1, wherein said method of tracking comprises fluorescent microscopy.

16. The method of claim 1 wherein the carrier is of formula:

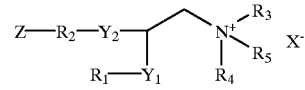

wherein $R_1$ is an aliphatic group having from 12 to about 20 carbon atoms or a steroid molecule;

$R_2$ is an aliphatic group having from 12 to about 20 carbon atoms;

$R_3$, $R_4$ are $CH_3$ or $CH_2CH_3$;

$R_5$ is $CH_3$, $(CH_2)_nCH_3$ where n=1 or 2, or $(CH_2)_nOH$ where n=1 to 5;

X is Br, I, or Cl;

$Y_1$, $Y_2$ are, independently, an ether, an ester, a carbamate, a peptide linkage, a carbonate, an amide, or a urea linkage; and Z is a label.

17. The method of claim 16 wherein said label is a fluorescent label.

18. A compound having the formula:

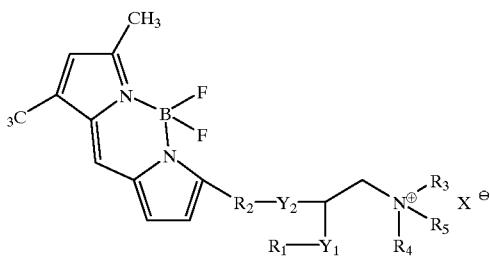

wherein $R_1$ is an aliphatic group having from 12 to about 20 carbon atoms or a steroid molecule;

$R_2$ is an aliphatic group having from 12 to about 20 carbon atoms;

$R_3$, $R_4$ are $CH_3$ or $CH_2CH_3$;

$R_5$ is $CH_3$, $(CH_2)_nCH_3$ where n=1 or 2, or $(CH_2)_nOH$ where n=1 to 5;

X is Br, I, or Cl; and $Y_1$, $Y_2$ are, independently, an ether, an ester, a carbamate, a peptide linkage, a carbonate, an amide, or a urea linkage.

19. The compound of claim 18, wherein $R_1$ is cholesterol.

20. The compound of claim 18, wherein X is Br.

21. The compound of claim 18, wherein $R_3$, $R_4$, and $R_5$ are $CH_3$, and $R_2$ is alkyl.

22. The compound of claim 18, wherein $R_1$ is alkyl and alkenyl.

23. The compound of claim 22, wherein $R_1$ is a straight chain alkenyl of about 17 carbons.

24. A compound having the formula:

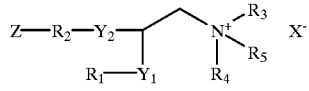

wherein $R_1$ is an aliphatic group having from 12 to about 20 carbon atoms or a steroid molecule;

$R_2$ is an aliphatic group having from 12 to about 20 carbon atoms;

$R_3$, $R_4$ are $CH_3$ or $CH_2CH_3$;

$R_5$ is $CH_3$, $(CH_2)_nCH_3$ where n=1 or 2, or $(CH_2)_nOH$ where n=1 to 5;

X is Br, I, or Cl;

$Y_1$, $Y_2$ are, independently, an ether, an ester, a carbamate, a peptide linkage, a carbonate, an amide, or a urea linkage; and Z is a label.

25. The compound of claim 24 wherein said label is a fluorescent label.

26. A process of making a fluorescently labeled cationic lipid comprising:

reacting a cationic lipid with a fluorescent dye to form a fluorescently labeled cationic lipid; and purifying said fluorescently labeled cationic lipid using radial chromatography.

27. The method of claim 7, wherein said first label is:

rhodamine;

3H-indolium-2-[3-[1-[6-[yl]-6-oxohexyl]-1,3-dihydro-3,3-dimethyl-5-sulfo-2H-indol-2-ylidene]-1-propenyl]-1-ethyl-3,3-dimethyl-5-sulfo;

3H-indolium-2-[5-[1-[6-[yl]-6-oxohexyl]-1,3-dihydro-3,3-dimethyl-5-sulfo-2H-indol-2-ylidene]-1,3-pentadienyl]-1-ethyl-3,3-dimethyl-5-sulfo;

1H, 5H, 11H, 15H-xantheno [[2,3,4-i'j':5,6,7-i'j'] diquinolizin-18-ium, 9-[2(or 4)-(sulfonyl)-4(or 2)-sulphenyl]-2,3,6,7,12,13,16,17-octahydro;

4,4-difluoro-5-yl-4-bora-3a,4a-diaza-s-indacenyl; or 4,4-difluoro-1,3-dimethyl-5-yl-4-bora-3a,4a-diaza-s-indacenyl.

* * * * *